United States Patent [19]

Drakesmith et al.

[11] Patent Number: 4,736,045

[45] Date of Patent: Apr. 5, 1988

[54] PROCESS FOR FLUORINATING ETHERS

[76] Inventors: Frederick G. Drakesmith, 5 Ffordd Argoed, Bryn Awelon, Mold, Clwyd, Wales; Richard L. Powell, 47 The Loont, Winsford, Cheshire, CW7 1EX; Richard D. Chambers, 5 Aykley Green, Whitesmocks, Durham DH1 4LN; Brian Grievson, Ivy Cottage, Waldridge Hall Farm, Waldridge Colliery, County Durham, all of United Kingdom

[21] Appl. No.: 652,560

[22] PCT Filed: Jan. 20, 1984

[86] PCT No.: PCT/GB84/00013

§ 371 Date: Sep. 11, 1984

§ 102(e) Date: Sep. 11, 1984

[87] PCT Pub. No.: WO84/02909

PCT Pub. Date: Aug. 2, 1984

[30] Foreign Application Priority Data

Jan. 20, 1983 [GB] United Kingdom ................. 8301506

[51] Int. Cl.$^4$ ................. C07D 319/12; C07D 307/48; C07C 43/11; C07C 43/12
[52] U.S. Cl. ................. 549/380; 549/428; 549/504; 549/511; 568/615; 568/683
[58] Field of Search ................. 204/158 HA; 568/615, 568/683; 549/380, 428, 504, 511

[56] References Cited

U.S. PATENT DOCUMENTS 2,644,823 7/1953 Kauck et al. ................. 260/345.1
3,816,286 6/1974 Haszeldine et al. ............. 204/163 R

OTHER PUBLICATIONS

Chambers et al., J. Fluorine Chemistry, 16(4), pp. 351–364 (1980).

*Primary Examiner*—Anton H. Sutto
*Attorney, Agent, or Firm*—Beveridge, DeGrandi & Weilacher

[57] ABSTRACT

Fluorinated ether, process for their preparation, and use of the fluorinated ethers as inert fluids.

18 Claims, No Drawings

PROCESS FOR FLUORINATING ETHERS

This invention relates to certain fluorinated ethers and to the use of the fluorinated ethers in a number of diverse fields, especially as inert fluids, for example the working fluid of a heat pump.

The invention relates to novel fluorinated ethers which are the product of a fluorination reaction of an adduct formed by the free-radical addition of a fluoro-olefin and a hydrogen-containing ether. The fluorinated ether may be partially or fully fluorinated during the fluorination reaction. The hydrogen-containing ether is preferably of the formula R—O—R' wherein R and R' are hydrocarbon groups optionally substituted by chlorine or fluorine or together form a single hydrocarbon group and the total number of carbon atoms in the groups R and R' is preferably less than 10; specifically groups R and R' may be the same or different and maybe selected from alkyl, cycloalkyl, aralkyl and aryl, provided that both groups are not aryl. The preferred alkyl groups are methyl, ethyl and propyl but may also be butyl or larger groups.

Among the preferred hydrogen-containing ethers which may be used in accordance with the present invention are dimethyl ether, diethyl ether, dipropyl ether, tetrahydrofuran, dioxane, tetrahydropyran, trimethylene oxide, or ethylene glycol dimethyl ether.

The preferred fluoro-olefin is tetrafluoro-ethylene. Other fluoro-olefins which may be used are difluoro-ethylene, chlorotrifluoroethylene, perfluorcyclobutene, trifluroethylene and hexafluoropropene. The mole ratio of the fluoro-olefin and the hydrogen-containing ether in the adduct may be from 6:1 to 1:1, but in certain instances may involve a larger amount of fluoro-olefin. For many working fluid applications, particularly for heat pump applications, it is preferred that the ratio of fluoro-olefin to the hydrogen-containing ether in the adduct is 2:1 or 1:1. The fluorinated ether according to the present invention may be one of the following compounds:

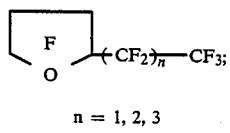

n = 1, 2, 3

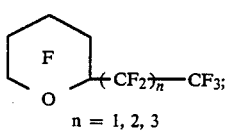

n = 1, 2, 3

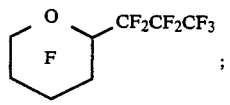

$CF_3CF_2OCFCF_3$
      |
      $CF_2CF_2CF_3$;

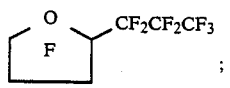

$CF_3CF—O—CFCF_3$
  |              |
$CF_3CF_2CF_2$  $CF_2CF_2CF_3$;

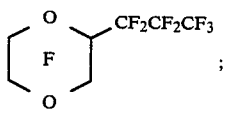

$CF_3CF_2CF_2OCFCF_2CF_3$
              |
              $CF_2CF_2CF_3$

In the above formulae the symbol F in the centre of the rings depicted indicates that all unmarked bonds are to fluorine atoms. This designation is used throughout the specification.

The present invention also includes a process for making fluorinated ethers as described above wherein the fluorination of the adduct is effected by the use of a high valency metal fluoride as a fluorinating agent at a temperature above 200° C. A fluorination procedure of this general kind is described in "Advances in Fluorine Chemistry" Vol. 1. Butterworth, 1960 P 166. Cobalt trifluoride alone or in association with alkali or alkaline earth metal fluorides such as potassium fluoride or calcium fluoride are the preferred fluorinating agents. In the process of this invention, the fluorination is preferably effected in the temperature range 300° C. to 600° C. eg. at temperatures between 400° C. to 500° C.

The present invention is concerned with compounds which have good stability and by suitable selection compounds are provided for use as inert fluids and in particular for the working fluid of a heat pump. Furthermore, compounds may be selected which are particularly useful as heat pipe fluids, as coolants, as heat absorption media eg. for geothermal heat recovery, as lubricants, in vapour phase soldering, as solvents, especially in the separation of ethyl alcohol from aqueous mixtures, or as dielectrics. Several of these uses require the fluorinated ether to have particularly high stability, which is a feature of the compounds of this invention. Furthermore, the use of partly fluorinated compounds as starting materials for the fluorination reaction in some cases substantially avoids, and not merely inhibits fragmentation of the adducts: additionally the fluorine containing adducts used in accordance with this invention permit controlled yields to be obtained with respect to various fluorinated ethers. It is known (see Journal of Fluorine Chemistry 1975 5 p 521-Brandwood, Coe, Ely and Tatlow) that the usual experience with fluorination of hydrocarbon material containing no fluorine is the production of a complicated mixture of fluorinated and partially fluorinated products, including the products of fragmentation. In using the process of this invention employing cobalt trifluoride as a fluorinating agent at elevated temperatures complete fluorination can be effected if the temperature employed is of the order of 440° C., for the adducts exemplified in this specification. The selection of lower temperatures, but above 200° C., results in the production of partially fluorinated ethers.

Fluorination with cobalt trifluoride is a technique well known in the art and is described in standard text books, for example R. D. Chambers "Fluorine in Organic Chemistry", see page 25. As is known, cobalt trifluoride can be re-generated by reacting elemental fluorine and the cobalt difluoride resulting from the organic fluorination reaction.

There is set out below a number of fluorination reactions in accordance with the present invention which have been carried out. All these fluorination reactions were effected, as indicated using cobalt trifluoride at 440° C.

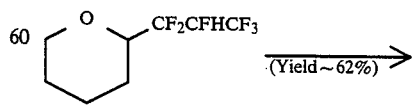

(Yield ~ 62%)

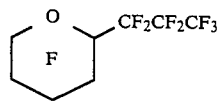

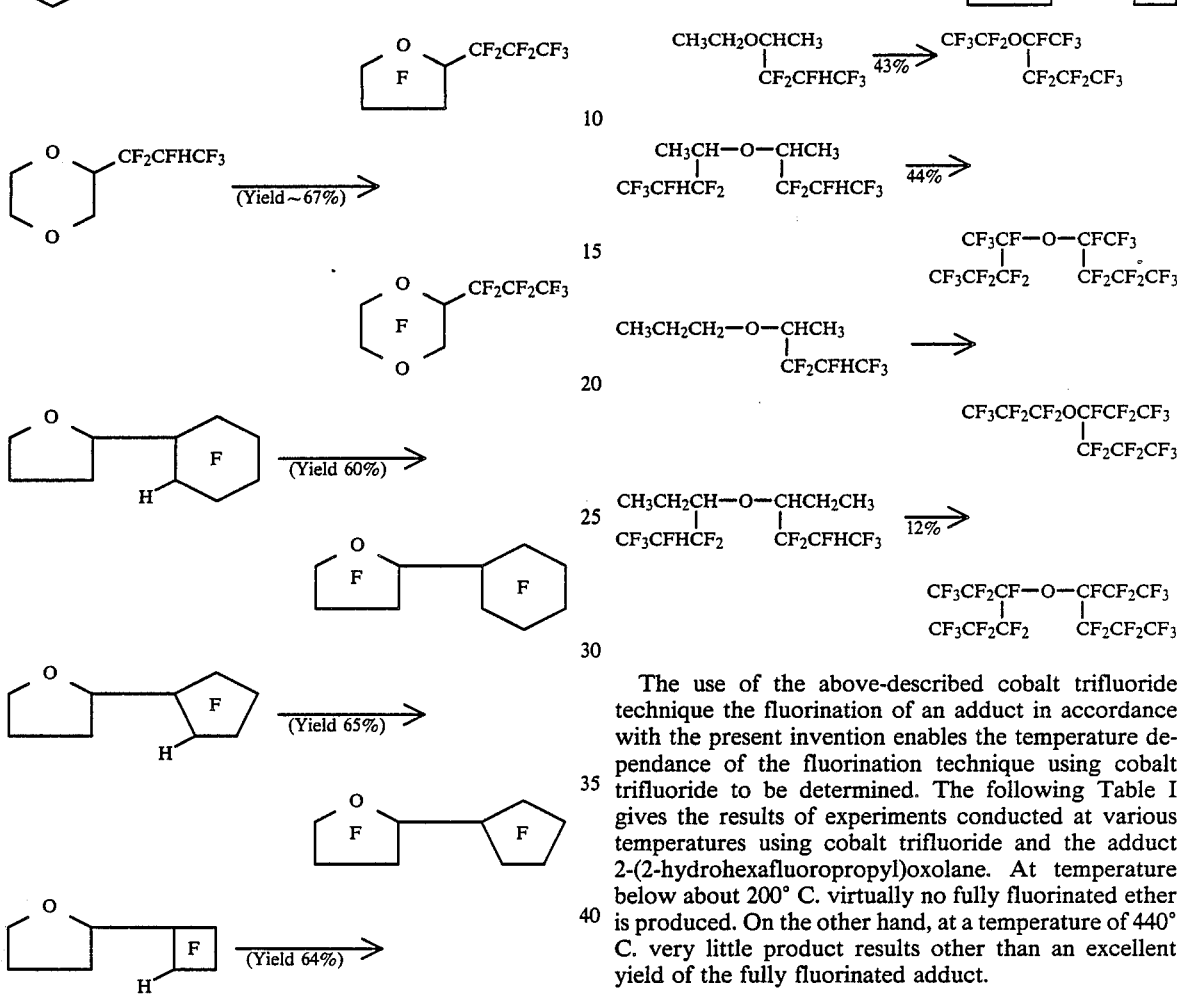

The use of the above-described cobalt trifluoride technique the fluorination of an adduct in accordance with the present invention enables the temperature dependance of the fluorination technique using cobalt trifluoride to be determined. The following Table I gives the results of experiments conducted at various temperatures using cobalt trifluoride and the adduct 2-(2-hydrohexafluoropropyl)oxolane. At temperature below about 200° C. virtually no fully fluorinated ether is produced. On the other hand, at a temperature of 440° C. very little product results other than an excellent yield of the fully fluorinated adduct.

TABLE I

Temperature Dependance of the Cobalt Trifluoride Fluorination of 2-(2-hydrohexafluoropropyl) oxolane

| % Yield | Temperature (°C.) | % $C_7F_{14}O$ | % $C_7F_{13}HO$ | % $C_7F_{12}H_2O$ | % $C_7F_{11}H_3O$ | % $C_7F_{10}H_4O$ and less-fluorinated derivatives |
|---|---|---|---|---|---|---|
| 30%[a] | 110 | trace | 1.3 | 3.7 | 23.3 | 71.1 |
| 49%[b] | 180 | trace | 1.5 | 7.5 | 69.8 | 21.3 |
| 79%[b] | 240 | 0.4 | 1.2 | 14.8 | 63.7 | 19.7 |
| 70%[c] | 270 | 2.8 | 20.9 | 29.2 | 42.9 | 2.4 |
| 73%[d] | 355 | 13.6 | 46.3 | 14.2 | 7.8 | — |

TABLE I-continued
Temperature Dependance of the Cobalt Trifluoride
Fluorination of 2-(2-hydrohexafluoropropyl) oxolane $$\text{oxolane-CF}_2\text{CFHCF}_3 \xrightarrow[\text{N}_2 \text{ CARRIER GAS (50 ml/min)}]{\text{CoF}_3}$$

| % Yield | Temperature (°C.) | % $C_7F_{14}O$ | % $C_7F_{13}HO$ | % $C_7F_{12}H_2O$ | % $C_7F_{11}H_3O$ | % $C_7F_{10}H_4O$ and less-fluorinated derivatives |
|---------|---|---|---|---|---|---|
| ~70%[e] | 440 | ~95% | ~1% | — | — | — |

[a]Based on $C_7F_6H_8O \longrightarrow C_7F_{10}H_4O$

[b]Based on $C_7F_6H_8O \longrightarrow C_7F_{11}H_3O$

[c]Based on $C_7F_6H_8O \longrightarrow C_7F_{12}H_2O$

[d]Based on $C_7F_6H_8O \longrightarrow C_7F_{13}HO$

[e]Based on $C_7F_6H_8O \longrightarrow C_7F_{14}O$

Pure samples of the component fluorinated ethers of the reaction mixture can be isolated by conventional techniques. It is possible to "tailor" a particular fluorinated ether for a particular use. However, it is also possible to prepare mixtures of materials, appropriate to specific uses, by one of the three following methods:
(a) Mixing pure components,
(b) Partial fluorination of a single adduct,
(c) Fluorination of mixed adducts.

The following Examples illustrate in detail the preparation of fluorinated ethers in accordance with the present invention.

EXAMPLE 1

Preparation of Perfluoro-2-Propyloxolane 2-(1,1,2,3,3,3,-hexafluoropropyl)oxolane was fluorinated with cobalt trifluoride/CaF₂ to produce perfluoro-2-propyloxolane (II) in good yield.

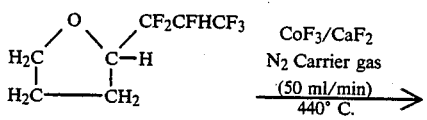

(I)

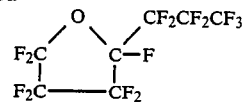

(II) 71%

Experimental Procedure

The fluorinating reagent (approx 330 g) was generated by passing fluorine gas through a bed composed of 150 g of cobalt difluoride and 150 g of calcium difluoride until fluorine was detected at the bed outlet using starch/iodide paper. Nitrogen gas was passed through the bed at 50 ml/min for 30 minutes at the required temperature of 440° C. The oxolane compound I (1.93 g, 8.7 mmol) was added dropwise at a rate of about 1 ml in 10 minutes, and the products collected in a trap cooled by liquid air. The bed was flushed out with nitrogen for 15 minutes. The trap was warmed up to room temperature, anhydrous sodium carbonate was added to remove dissolved hydrogen fluoride, and the colourless liquid (2.27 g) separated. The liquid was distilled at atmospheric pressure to give perfluoro-2-propyl-oxolane, Bpt 79° C., with a yield of 71%.

EXAMPLE 2

The addition of a variety of ethers (I) to the fluoroalkenes (II) was carried out using γ-ray initiation of the reaction at ambient temperature to give the adduct (III), or a mixture of such adducts. The adduct(s) (III) were separated, purified and individually fluorinated using a cobalt trifluoride catalyst at a temperature of 440° C. to give a variety of perfluoroethers (IV) and by-products (V). The results are summarised in Table II:

TABLE II
ADDITION OF ETHERS TO PERFLUOROALKENES AND FLUORINATION TO PRODUCE PERFLUOROETHERS $$R^aCH_2\underset{\underset{(I)}{CH_2R^b}}{\overset{O}{\diagdown\diagup}} \xrightarrow[\gamma, 18°C.]{R_fCF=CFR_f'\ (II)} H(R_fCFCFR_f')_p\underset{\underset{R^b}{CH(CFR_fCFR_f')_qH}}{\overset{O}{\diagdown\diagup}}\underset{R^a}{CH} \xrightarrow[440°C.]{CoF_3} F(R_fCFCFR_f')_p\underset{\underset{R_f^b}{CF(CFR_fCFR_f')_qF}}{\overset{O}{\diagdown\diagup}}\underset{R_f^a}{CF} + \text{BY-PRODUCTS (V)}$$

(III)   (IV)

where $R_f^a$ and $R_f^b$ represent the groups $R^a$ and $R^b$ respectively with all the hydrogen atoms replaced by fluorine.

| STARTING ETHER (I) | PERFLUORO-ALKENE (II) | ADDUCT (III) | % YIELD (III) | PERFLUORO-ETHER (IV) | % YIELD (IV) | Bpt (IV) | BY PRODUCTS (V) | % YIELD (V) | EXPERIMENT NUMBER |
|---|---|---|---|---|---|---|---|---|---|
| $(CH_3)_2O$ | $CF_2=CFCF_3$ | $p=1, q=0$ | 68 | $p=1, q=0$ | 36 | — | $CF_3(CF_2)_2CF_3$ | 44 | 1 |
|  | ⬡F | $p=1, q=0$ | 78 | $p=1, q=0$ | 16 | — | ⬡-CF₃ F | 9 | 2 |
|  | ▢F | $p=1, q=0$ | 74 | Complex mixture of Products |  |  |  |  | 3 |
| $(CH_3CH_2)_2O$ | $CF_2=CFCF_3$ | $p=1, q=0$ | 38 | $p=1, q=0$ | 43 | 78 | $CF_3(CF_2)_3CF_3$ | 10 | 4 |
|  | $CF_2=CFCF_3$ | $p=1, q=1$ | 43 | $p=1, q=1$ | 41 | 136 | $CF_3(CF_2)_3CF_3$ | 9 | 5 |
| $(CH_3CH_2CH_2)_2O$ | $CF_2=CFCF_3$ | $p=1, q=0$ | 12 | $p=1, q=0$ | 32 | 137 | — | — | 6 |
|  | $CF_2=CFCF_3$ | $p=1, q=1$ | 28 | $p=1, q=1$ | 12 | 162 | $CF_3(CF_2)_4CF_3$ | 30 | 7 |
| $(CH_3CH_2CH_2CH_2)_2O$ | $CF_2=CFCF_3$ | $p=1, q=0$ | 16 | $p=1, q=0$ | 18 | 149 | $CF_3(CF_2)_5CF_3$ | 10 | 8 |
|  | $CF_2=CFCF_3$ | $p=1, q=1$ | 28 | — | — | — | $CF_3(CF_2)_5CF_3$ | 32 | 9 |
| $(CH_3OCH_2)_2$ | $CF_2=CFCF_3$ | $CH_3OCHCH_2OCH_3$ $\|$ $CF_2CFHCF_3$ | 53 | Complex mixture of Products |  |  |  |  | 10 |
| ▢O | $CF_2=CFCF_3$ | $p=1, q=0$ | 65 | $p=1, q=0$ | 8 | — | $CF_3(CF_2)_4CF_3$ $CF_3(CF_2)_3CF_3$ | 10 3 | 11 |
| ⬠O | $CF_2=CFCF_3$ | $p=1, q=0$ | 95 | $p=1, q=0$ | 70 | 79 | $CF_3(CF_2)_4CF_3$ | 5 | 12 |
|  | $CF_3CF=CFCF_3$ | $p=1, q=0$ | 89 | $p=1, q=0$ | 53 | 101 | — | — | 13 |
|  | $CF_2=CFCl$ | $p=1, q=0$, $R_f'=Cl$ | 78 | $p=1, q=0$, $R_f'=Cl$ | 45 | 82 | — | — | 14 |
|  |  |  |  | $p=1, q=0$, $R_f'=F$ | 12 | 54 |  |  |  |
| ⬠O F | $CF_2=CFCF_3$ | $p=1, q=0$ | 91 | $p=1, q=0$ | 64 | — | — | — | 15 |

TABLE II-continued
ADDITION OF ETHERS TO PERFLUOROALKENES AND FLUORINATION TO PRODUCE PERFLUOROETHERS $$R^aCH_2\underset{CH_2R^b}{\underset{|}{O}}\xrightarrow[\gamma, 18°C.]{R_fCF=CFR_f\ (II)} H(R_fCFCFR_f)_pCH\underset{R^b}{\underset{|}{\underset{O}{|}}}CH(CFR_fCFR_f)_qH \xrightarrow[440°C.]{CoF_3} F(R_fCFCFR_f)_pCF\underset{R_f^b}{\underset{|}{\underset{O}{|}}}CF(CFR_fCFR_f)_qF + \text{BY-PRODUCTS (V)}$$

(I)          (III)          (IV)

where $R_f^a$ and $R_f^b$ represent the groups $R^a$ and $R^b$ respectively with all the hydrogen atoms replaced by fluorine.

| STARTING ETHER (I) | PERFLUORO- ALKENE (II) | ADDUCT (III) | % YIELD (III) | PERFLUORO- ETHER (IV) | % YIELD (IV) | Bpt (IV) | BY PRODUCTS (V) | % YIELD (V) | EXPERIMENT NUMBER |
|---|---|---|---|---|---|---|---|---|---|
|  |  | p = 1, q = 0 | 83 | p = 1, q = 0 | 65 | 117 |  | 11 | 16 |
| |  | p = 1, q = 0 | 91 | p = 1, q = 0 | 51 | 136 |  | 6 | 17 |
| | 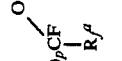 |  | 89 | 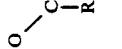 | 16 | — | — | — | 18 |
| | CF$_2$=CFCF$_3$ | p = 1, q = 0 | 61 |  | 15 | 101 | — | — | 19 |
|  | 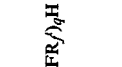 | p = 1, q = 0 | 76 | p = 1, q = 0 | 62 | — | — | — | 19 |
| | | | | p = 1, q = 0 | 31 | 134 |  | 20 | 20 |

TABLE II-continued
ADDITION OF ETHERS TO PERFLUOROALKENES AND FLUORINATION TO PRODUCE PERFLUOROETHERS $$R^aCH_2\underset{(I)}{\overset{O}{\diagdown}}CH_2R^b \xrightarrow[\gamma, 18°\text{ C.}]{R_fCF=CFR_f\ (II)} H(R_fCFCFR_f)_pCH\underset{R^a}{\overset{O}{\diagdown}}CH(CFR_fCFR_f)_qH \xrightarrow[440°\text{ C.}]{CoF_3} F(R_fCFCFR_f)_pCF\underset{R_f^a}{\overset{O}{\diagdown}}CF(CFR_fCFR_f)_qF + \text{BY-PRODUCTS (V)}$$

$$\text{(III)} \qquad \text{(IV)}$$

where $R_f{}^a$ and $R_f{}^b$ represent the groups $R^a$ and $R^b$ respectively with all the hydrogen atoms replaced by fluorine.

| STARTING ETHER (I) | PERFLUORO- ALKENE (II) | ADDUCT (III) | % YIELD (III) | PERFLUORO- ETHER (IV) | % YIELD (IV) | Bpt (IV) | BY PRODUCTS (V) | % YIELD (V) | EXPERIMENT NUMBER |
|---|---|---|---|---|---|---|---|---|---|
| 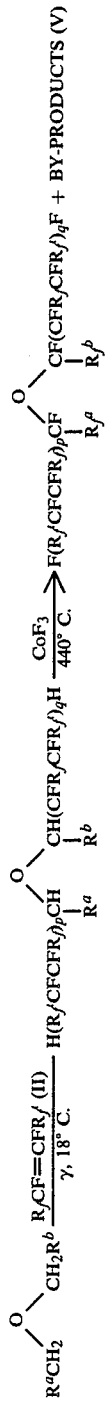 | $CF_2=CFCF_3$ | $p=1, q=0$ | 79 | $p=1, q=0$ | 68 | 90 | — | — | 21 |
| | cyclopentene-F | $p=1, q=0$ | 49 | $p=1, q=0$ | 17 | 125 | cyclopentane-F with $CF_2CF_2OCF_3$ | 8 | 22 |
| | | | | | | | cyclopentane-F with $CF_2CF_3$ | 10 | 22 |
| | $CF_2=CFCF_3$ | $p=1, q=0$ | 70 | $p=1, q=0$ | 45 | 124 | $CF_3(CF_2)_6CF_3$ | 12 | 23 |
| | cyclopentene-F | $p=1, q=0$ | 71 | $p=1, q=0$ | 20 | 158 | cyclopentane-F with $CF_2(CF_2)_3CF_3$ | 22 | 24 |
|  | $CF_2=CFCF_3$ | 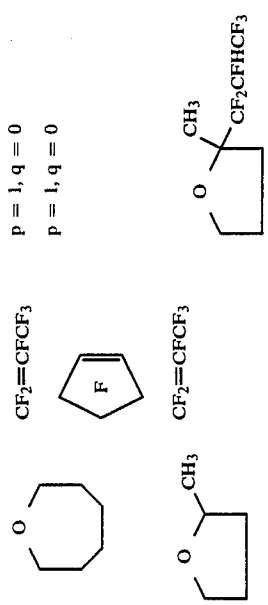 | 96 | perfluoro-THF with $CF_3$, $CF_2CF_2CF_3$ | 18 | 101 | $CF_3CF_2CF(CF_2)_2CF_3$ with $CF_3$ | 10 | 25 |
| | | | | perfluoro-THF with $CF_3$, $CF_2CF_2CF_3$ | 25 | 94 | | | 25 |

EXAMPLE 3

The addition of a variety of ethers (I) to tetrafluoroethene ($CF_2$=$CF_2$) was carried out using a tertiary butyl peroxide catalyst at a temperature of 140° C. in an autoclave. Each ether (I) gave a mixture of adducts (VI) which were separated and fluorinated individually using a cobalt trifluoride catalyst at a temperature of 440° C. to give the perfluoroethers (VII). The results are summarised in Table III:

EXAMPLE 4

Dimethyl ether was added to trifluoroethene by a free-radical reaction using a tertiary butyl peroxide catalyst at a temperature of 140° C. in an autoclave. The product mixture was separated into the adduct isomer mixtures (VIII) which were fluorinated using a cobalt trifluoride catalyst at a temperature of 440° C. to give the perfluoroethers (IX) the by-products (X). The results are summarised in Table (IV):

TABLE III
ADDITION OF ETHERS TO TETRAFLUOROETHENE AND FLUORINATION TO PRODUCE PERFLUOROETHERS

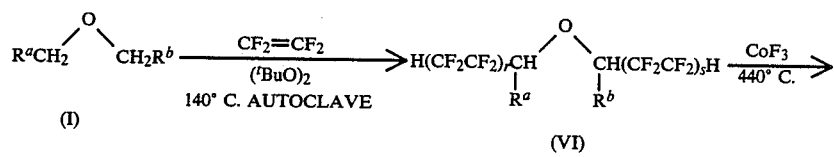

(I) → (VI)

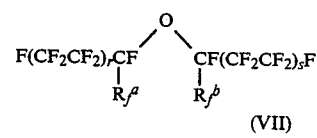

(VII)

where $R_f^a$ and $R_f^b$ represent the groups $R^a$ and $R^b$ respectively with all the hydrogen atoms replaced by fluorine.

| STARTING ETHER (I) | ADDUCT (VI) | % YIELD (VI) | PERFLUOROETHER (VII) | % YIELD (VII) | Bpt (°C.) (VII) | EXPERIMENT NUMBER |
|---|---|---|---|---|---|---|
| ⌷O⌷ | r = 1, s = 0 | 61 | r = 1, s = 0 | 65 | 54 | 1 |
|  | r + s = 2 | 30 | r = 1, s = 1 | } 65–70 | 93 | 2 |
|  |  |  | r = 2, s = 0 |  | — |  |
|  | r + s = 3 | 8 | r = 2, s = 1 | } 61 | 132 | 3 |
|  |  |  | r = 3, s = 0 |  | 141 |  |
|  | r = s = 4 | 0.8 | r = 3, s = 1 | } 55 | — | 4 |
|  |  |  | r = 4, s = 0 |  | — |  |
| O⌷O | r = 1, s = 0 | 57 | r = 1, s = 0 | 33 | 65 | 5 |
|  | r + s = 2 | 30 | r = 1, s = 1 | } 34 | 103 | 6 |
|  |  |  | r = 2, s = 0 |  | 110 |  |
|  | r + s = 3 | 11 | r = 2, s = 1 | } 38 | 141 | 7 |
|  |  |  | r = 3, s = 0 |  | 150 |  |
|  | r + s = 4 | 2 | r = 3, s = 1 | } 35 | 174 | 8 |
|  |  |  | r = 4, s = 0 |  | 180 |  |
| $(CH_3CH_2)_2O$ | r = 1, s = 0 | 51 | r = 1, s = 0 | 23 | 56 | 9 |
|  | r + s = 2 | 37 | r + s = 2 | 31 | 98 | 10 |
|  | r + s = 3 | 10 | r + s = 3 | 35 | — | 11 |
|  | r + s = 4 | 2 | r + s = 4 | 35 | — | 12 |

TABLE IV

ADDITION OF DIMETHYLETHER TO TRIFLUOROETHENE AND FLUORINATION TO PRODUCE PERFLUOROETHERS

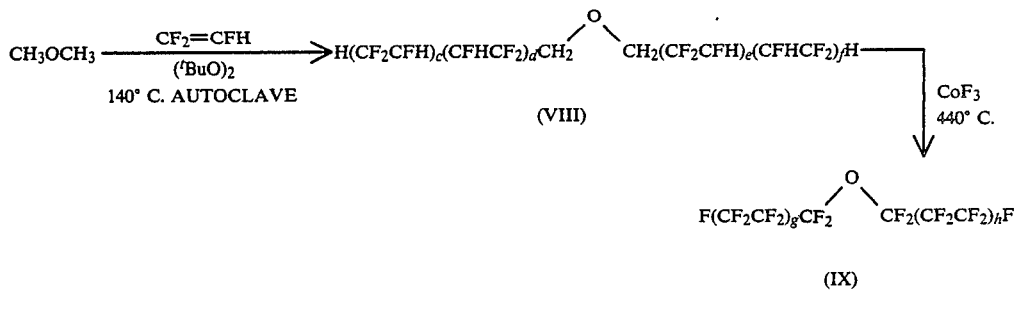

| ADDUCT (VIII) | % YIELD (VIII) | PERFLUOROETHER (IX) | % YIELD (IX) | Bpt (IX) (°C.) | BY-PRODUCTS (X) | % YIELD (X) | EXPERIMENT NUMBER |
|---|---|---|---|---|---|---|---|
| c + d + e + f = 1 | 62 | UNIDENTIFIED MIXTURE OF PERFLUORINATED PRODUCTS | | | | | 1 |
| c + d + e + f = 2 | 30 | g = 2, h = 0 | 14 | 62 | — | — | 2 |
| c = d = e = f = 3 | 6 | g = 3, h = 0 | 7 | 106 | CF$_3$(CF$_2$)$_4$CF$_3$ | 29 | 3 |
| | | g = 2, h = 1 | 3 | — | CF$_3$(CF$_2$)$_5$CF$_3$ | 12 | |

It is to be understood that in making the novel fluorinated ethers according to the present invention other techniques for fluorinating the adducts may be employed, for example elemental fluorine or ClF$_3$ or electrochemical fluorination may be employed.

In many working fluid situations the working fluid is exposed to cyclic temperature changes, and the fluorinated ethers according to this invention provide compounds or mixes of compounds which are suitable for this purpose. The fluorinated ethers may be employed in an apparatus in which there is transfer of heat from a higher to a lower temperature, or alternatively in an apparatus where there is transfer of heat from a lower to a higher temperature. Furthermore, it is to be noted that the fluorinated ethers may be used in apparatus in which there is a change from a liquid to a vapour state, and back to the liquid state, such as is the case with the heat pump. A particular use where a change of state is involved is in using these working fluids in a refrigerator: another use is in the transfer of heat in chemical reactors and the like. One particular situation where the fluorinated ethers of this invention may be used with advantage is in the generation of power, for example Organic Rankine Cycle power generation or the abstraction of heat from geothermal sources, including the conversion of geothermal energy to work.

The compounds or mixtures of compounds according to the invention for use as the working fluid in a heat pump may be chosen so as to provide the desired critical temperature and boiling point. Other factors are relevant, but these are the prime ones. The critical temperature and boiling point desired will depend upon the condensing and evaporating temperatures used in the heat pump.

A suitable substance for use as a working fluid in a heat pump condensing at $T_C$ and evaporating at $T_E$ would have a critical temperature substantially higher than $T_C$ and a normal boiling point substantially lower than $T_E$. Thus for example, if $T_C = 150°$ C. and $T_E = 100°$ C., a possible working fluid would be 1.1.1.2.3.3. hexafluoro butyl methyl ether which has a critical temperature of 236° C. and a normal boiling point of 87° C., or perfluoro-2-propyloxolane which has a critical temperature of 206° C. and a normal boiling point of 79° C.

Adducts formed by reacting tetrafluoroethylene (CF$_2$=CF$_2$) with hydrogen containing, eg. hydrocarbon, ethers are formed as mixtures of products. The reaction tends to produce telomers of the type H (CF$_2$—CF$_2$)$_n$—R O R' where n may be from 1 to well above 8. Fluorination of these telomer mixtures can produce mixtures of compounds according to the invention having boiling points, critical temperatures and other properties suiting them for particular uses. For instance, when tetrafluoroethylene is reacted to add to tetrahydrofuran the products after fluorination have the formula:

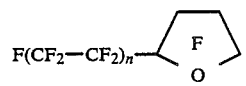

Products are obtained which are useful, for example, as follows:
for low values of n—working fluids and coolants,
intermediate values of n—fluids for vapour phase soldering, and
higher values of n—lubricants

We claim:
1. A process for the preparation of a fully fluorinated ether, wherein the process comprises
   forming an adduct comprising a free-radical addition of a fluoro-olefin and a hydrogen-containing ether; and
   fluorinating the adduct using cobalt trifluoride as a fluorinating agent at a temperature of 300° to 600° C. and substantially avoiding fragmentation of said adduct and thereby controlling the yield of the desired fluorinated ether.
2. A process as claimed in claim 1, wherein the hydrogen-containing ether used in the formation of the adduct is of the formula R—O—R' wherein R and R' are hydrocarbon groups or together form a single hydrocarbon group and the total number of carbon atoms in the hydrocarbon groups R and R' is up to 10.

3. A process as claimed in claim 2, wherein the groups R and R' are the same or different and are selected from the group consisting of methyl, ethyl, propyl and butyl groups.

4. A process as claimed in claim 1, wherein the hydrogen-containing ether used in the formation of the adduct is of the formula R—O—R' wherein R and R' are halogen containing hydrocarbon groups.

5. A process as claimed in claim 1, wherein the fluoro-olefin used in the formation of the adduct is selected from the group consisting of tetrafluoroethylene and hexafluoropropene.

6. A process as claimed in claim 1, wherein the hydrogen-containing ether used in the formulation of the adduct is selected from the group consisting of dimethyl ether, diethyl ether, dipropyl ether, tetrahydrofuran, dioxane, tetrahydrogpyran, trimethylene oxide and ethylene glycol dimethyl ether.

7. A process as claimed in claim 1, wherein the fluorination is effected using a mixture of cobalt trifluoride and potassium fluoride as the fluorinating agent.

8. A process as claimed in claim 7, wherein the temperature employed is in the range of from 400° C. to 450° C.

9. A process as claimed in claim 1, wherein the mole ratio of the fluoro-olefin to the hydrogen-containing ether in the adduct is 6:1 to 1:1.

10. A process as claimed in claim 1, wherein the mole ratio of the fluoro-olefin to the hydrogen-containing ether in the adduct is 2:1 to 1:1.

11. Process as claimed in claim 1, wherein the adduct is fluorinated at a temperature of 400° to 500° C.

12. Process as claimed in claim 1, wherein the adduct is fluorinated at a temperature in the range of from 400° to 450° C.

13. Process as claimed in claim 1, wherein the adduct is fluorinated at a temperature of about 440° C.

14. A process for the preparation of a fully fluorinated ether, wherein the process comprises
    forming an adduct comprising free-radical addition of a fluoro-olefin and a hydrogen-containing ether, wherein the mole ratio of fluoro-olefin to hydrogen-containing ether in the adduct is from 6:1 to 1:1;
    fluorinating the adduct using a fluorinating agent comprising cobalt trifluoride at a temperature of 300° to 600° C.;
    wherein the fluoro-olefin is selected from the group consisting of difluoroethylene, trifluoroethylene, tetrafluoroethylene, chlorotrifluoroethylene, hexafluoropropene and perfluorocyclobutene; and
    wherein the hydrogen-containing ether is selected from the group consisting of dimethyl ether, diethyl ether, dipropyl ether, tetrahydrofuran, dioxane, tetrahydropyran, trimethylene oxide and ethylene glycol dimethyl ether, and substantially avoiding fragmentation of said adduct and thereby controlling the yield of the desired fluorinated ether.

15. Process as claimed in claim 14, wherein the fully fluorinated ether is in a mixture of fluorinated ethers in which at least one ether in the mixture is fully fluorinated.

16. Process as claimed in claim 14, wherein the adduct is fluorinated at a temperature of 400° to 500° C.

17. Process as claimed in claim 16, wherein the fluorinating agent consists essentially of a mixture of cobalt trifluoride and potassium fluoride.

18. Process as claimed in claim 14, wherein the adduct is fluorinated at a temperature in the range of from 400° to 450° C.

* * * * *